(12) United States Patent
Pavini

(10) Patent No.: US 11,622,879 B2
(45) Date of Patent: Apr. 11, 2023

(54) PROTECTIVE AND EXERCISE HAND RESTRAINT SYSTEM AND APPARATUS

(71) Applicant: Marie Pavini, Chittenden, VT (US)

(72) Inventor: Marie Pavini, Chittenden, VT (US)

( * ) Notice: Subject to any disclaimer, the term of this patent is extended or adjusted under 35 U.S.C. 154(b) by 9 days.

(21) Appl. No.: 16/956,882

(22) PCT Filed: Dec. 7, 2018

(86) PCT No.: PCT/US2018/064618
§ 371 (c)(1),
(2) Date: Jun. 22, 2020

(87) PCT Pub. No.: WO2019/113548
PCT Pub. Date: Jun. 13, 2019

(65) Prior Publication Data
US 2021/0100676 A1    Apr. 8, 2021

Related U.S. Application Data

(60) Provisional application No. 62/595,783, filed on Dec. 7, 2017.

(51) Int. Cl.
*A61F 5/37* (2006.01)
*A63B 21/00* (2006.01)

(52) U.S. Cl.
CPC .......... *A61F 5/3761* (2013.01); *A61F 5/3776* (2013.01); *A63B 21/4019* (2015.10)

(58) Field of Classification Search
CPC ........ A61F 15/004; A61F 13/041; A61F 5/01; A61F 5/0118; A61F 13/00068; A61F 13/06; A61F 13/085; A61F 13/104; A61F 15/002; A61F 5/05; A61F 13/00038; A61F 13/0269; A61F 13/0273; A61F 13/04; A61F 13/107; A61F 13/108; A61F 15/006; A61F 2013/00119; A61F 2013/0054; A61F 2013/00565; A61F 2013/00889;
(Continued)

(56) References Cited

U.S. PATENT DOCUMENTS 2,237,252 A * 4/1941 Longfellow ........... A61G 7/075
   602/20
3,722,508 A * 3/1973 Roberts .................. A61M 5/52
   128/877
(Continued)

FOREIGN PATENT DOCUMENTS

CN    206630750 U    11/2017

OTHER PUBLICATIONS

International Search Report and Written Opinion dated Mar. 4, 2019, in connection with PCT/US2018/064618, filed Dec. 7, 2018.

*Primary Examiner* — Ophelia A Hawthorne
(74) *Attorney, Agent, or Firm* — Downs Rachlin Martin PLLC

(57) ABSTRACT

Embodiments disclosed herein offer protective restraint of the hand by securing it with a wrist tie to a padded transparent hard-shell hand restraint with wrist tie slots, multiple ventilation holes, a detachable flexible soft under wrap and a hinging ball-bearing style attachment point for optional attachment to a restraint arm rod and staff-directed upward displacement for enhanced access to the hand, and slots for a resistance band tie for enhanced exercise and intermediate level of restraint and a rigid tie.

12 Claims, 6 Drawing Sheets

(58) Field of Classification Search
CPC .... A61F 5/0109; A61F 5/0111; A61F 5/0585; A61F 5/3761; A61F 5/05866; A61F 5/37; A61F 5/3723; A61F 5/3769; A61F 2007/0035; A61F 5/05858; A61F 5/373; A61F 5/3776

See application file for complete search history.

(56) References Cited

U.S. PATENT DOCUMENTS

| | | | |
|---|---|---|---|
| 2002/0092528 A1* | 7/2002 | Chapman | E05B 75/00 128/869 |
| 2015/0237925 A1* | 8/2015 | Sewell | A41D 13/00 2/455 |
| 2017/0112656 A1 | 4/2017 | Maynard | |

* cited by examiner

PROTECTIVE AND EXERCISE HAND RESTRAINT SYSTEM AND APPARATUS

FIELD OF THE INVENTION

The present invention generally relates to the field of medical protective devices and restraints. In particular, the present invention is directed to protective and exercise hand restraints and related patient restraint and exercise methods.

BACKGROUND

For intubated intensive care unit patients confined to a bed for any significant period of time, meaningful early mobilization and sedation minimization are key elements in reducing morbidity and mortality, hastening recovery and improving quality of life by preserving cognition and strength. However, when endotracheal tubes (ETT) or other breathing tubes, naso/orogastric tubes, intravenous (IV) lines and other medical devices are in place, preventing removal (e.g. self-extubation) of such devices can also reduce morbidity and mortality in the ICU. In order to prevent removal, restraints that drastically restrict the patient's range of motion are used and sedation is then administered to reduce the anxiety of being unable to move. Caregiver personnel are reluctant to loosen or remove restraints because of the dire consequences of premature medical device disconnection thereby presenting a dilemma in balancing these competing concerns.

Various types of restraints have been employed in an attempt to permit a reasonable range of motion while still protecting against device removal by the patient. However, existing restraint systems that do allow for reasonable motion still do not provide reliable or sufficient protection against device removal. For example, mitt restraints are often ineffective as patients can still disconnect themselves by pressing the mitts together. Other problems with this type of restraint include circumferential binding at the wrist, obscured or delayed access of hand IV sites, wrist arterial line sites and continual circulation monitoring. With wrist restraints, if patients are awake, as is often desirable, they may be able to move a tube they want to disconnect toward the tied hand rather than the hand to the tube. Often this is done in a state of stupor, but any further awakening of the patient can cause extreme anxiety with the realization that they are tied to a bed. Other problems with this type of restraint include hand edema, arterial and venous compression as it is not readily visible when the restraint becomes too tight. Elbow immobilizers or arm boards are also employed, but awake patients may be able to disconnect themselves from such restraints. Other problems with these types of restraints include obscuring of IV sites, nerve palsies and creation or worsening of pressure sores. Difficulties with existing systems can burden the ICU staff, who may be required to spend more time watching one patient to the detriment of another and to their documentation and medication dispersion duties. Embodiments disclosed herein provide restraint systems that allow an awake patient to move their arms while reducing the likelihood of or prohibiting self-extubation.

SUMMARY OF THE DISCLOSURE

Disclosed embodiments help to prevent self-extubation of the ETT of an awake patient who may reflexively attempt removal, but also allow early mobilization and exercise necessary for preservation of as much muscle strength as possible, promotion of diaphragmatic motion necessary for liberation from the ventilator and reduction of patient stress from not being tied to the bed, allowing for sedation minimization and improved cognition. The disclosed embodiments contain a patient's hands to disallow self-removal of vital tubes and lines. Embodiments may also attach to such substrates as the wrist portion of a patient restraint arm rod in other restraint systems. or any other substrate with the same intended purpose or as a separate component, or may be used in conjunction with guard devices disclosed in Applicant's co-pending international application entitled: ENDOTRACHEAL TUBE GUARD WITH OPTIONAL HOLDING SYSTEM AND OPTIONAL SENSOR, application no. PCT/US18/64603, filed concurrently herewith (hereinafter, "ENDOTRACHEAL TUBE GUARD application", which is incorporated by reference), to prevent self-extubation.

Embodiments disclosed herein offer protective restraint of the hand by securing it with a wrist tie to a padded transparent hard-shell hand cage with wrist tie slots, multiple ventilation holes, a detachable flexible soft under wrap and a hinging ball-bearing style attachment point for optional attachment to the protective and exercise restraint and staff-directed upward displacement for enhanced access to the hand, and slots for a resistance band tie for enhanced exercise and intermediate level of restraint and a rigid tie when used alone or in conjunction with the devices disclosed in Applicant's aforementioned ENDOTRACHEAL TUBE GUARD application for optional strict restraint. The diameter of the hand cage may vary from proximal to distal ends to assure noncontact with the encased hand. This disclosure includes a dual slot embodiment configured to allow maximal crossing of the wrist tie at the anterior wrist, such that self-removal of the hand is prohibited. The cage is large enough such that when the encased hand is at rest on a surface, the hand cage is not in contact with the skin so as to avoid trauma to the skin of the hand in at-risk patients, such as from skin breakdown when used for typical lengths of time required for intubated patients, by providing minimal skin contact. Also disclosed is a single slot embodiment. Embodiments disclosed include a hand restraint, which is secured in such a way as to disallow self-removal while providing rotational movement of the wrist, limited movement of the hand and visualization and access to the hand while refraining from circumferential banding of the wrist. Embodiments of the disclosed hand restraint provide continual visualization and instant nursing access to the hand intravenous or wrist intra-arterial lines, skin assessment and nailbed circulation assessment as well as patient hand usage such as communication, therapy and hand-holding.

Embodiments of systems disclosed herein may be used in conjunction with devices disclosed in the ENDOTRACHEAL TUBE GUARD application for increased hindrance of self-extubation; may include a resistance band tie for resistance exercise and/or an intermediate level of restraint which can be interchanged with resistance band ties of varying tensile strength to offer variable degrees of exercise and restraint; may include a rigid tie for a strict level of restraint; may include a wrist tie spacer inside the hand cage for prevention of hand contact with the hand cage; and/or maybe utilized with most child to adult hand sizes. Disclosed systems allow for enhanced patient participation in early mobilization, potentially reduced sedation thereby reducing the risk of delirium while helping to assure that the then awake patient cannot disengage the device, increased thoracic exercise for diaphragmatic strength and secretion clearance thereby hastening recovery from the ventilator and minimize pressure sores and skin breakdown, all in a manner which reduces staff monitoring requirements for prevention of self-extubation. Disclosed embodiments include a wrist strap that wraps in such a way as to render the wrist available for an arterial line and the back of the hand for IV lines, while disallowing patient removal and refraining from circumferential binding of superficial arteries. A flexible soft detachable under wrap assures the hand is prohibited from reaching outside the hand cage to engage medical tubes, lines or catheters while offering no harder resting surface for the hand than the surface underneath the under wrap. Easy detachability assures quick access by medical personnel for physical examination and access.

A dual slot embodiment allows a wrist tie to encase the wrist and thread through the hand cage through two slots such that the angle of crossing at the anterior wrist is smaller than when threaded through a single slot. In both the dual and single slot embodiments, an adjustable securing mechanism on the outside of the hand cage secures any size hand in the wrist tie such that the wrist loop is too small to retract the hand through for disengagement.

Disclosed embodiments may include an optional wireless activity sensor to monitor anxiety and agitation based upon the quickness of patient arm movements which is transmitted to a screen that outputs color and/or picture symbol signals to indicate hypoactive movement, normoactive movement and hyperactive agitated movement for staff monitoring to guide intervention. Disclosed embodiments also may include an optional wireless activity sensor to allow for patient interactive video therapy game involvement such that activating the sensor with a switch pad causes a result within the video therapy game.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

DETAILED DESCRIPTION

Figure 1:
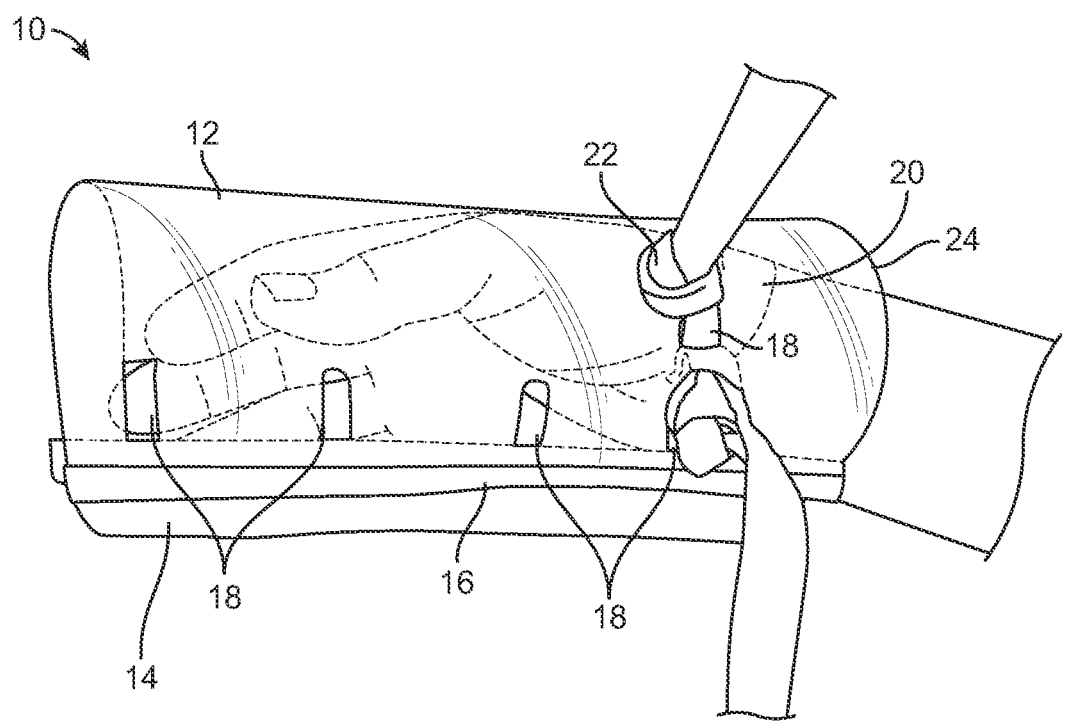
FIG. 1 is a photograph of the protective and exercise hand restraint as viewed from the right-handed medial palmar side of the double slot embodiment made in accordance with the present disclosure.

A first embodiment of a protective and exercise hand restraint 10 is shown in FIGS. 1-5. As shown therein, restraint 10 includes clear outer protective cover 12, which may be ventilated to provide airflow around the patient's hand. Across the bottom, inside cover 12 is detachable soft hand support 14 (under wrap). Hand support 14, for example, may comprise neoprene sheet or other similar atraumatic, resilient and washable material. Cover 12 and soft hand support 14 should be sized to allow sufficient space around the hand not only for air flow and to avoid rubbing against the sides of the cover, but also to permit access to the patient's fingers and back of the hand by medical personnel so as to be able to place or remove devices such as finger-attached pulse ox sensor, or IVs. Also finger sticks for small blood draws are possible without removing restraint 10.

Slots 18 are provided in the sides of cover 12 to permit adjustable ties such as wrist tie 20 to extend there through for securing restraint 10 in place around the patient's hand. In one embodiment, wrist straps 20 may be secured with adjustable slip connectors 22, which are easy for medical personnel to operate with two hands but cannot be shaken loose by the patient. Wrist straps 20 provide a safe, non-skin irritating means of securing restraint 10. As shown in more detail in FIG. 10, a noose-type configuration in which strap 20a is passed through a small permanent loop 20b at one end to form a larger slip or "noose-like" loop through which the hand is placed is preferred for most clinical situations. Such a "noose-like" slip loop tightens when the patient attempts to withdraw the hand, but then loosens again on its own when the hand is moved forward so as to minimize negative impacts on circulation and skin integrity. Strap 20a, like other straps 20 disclosed herein, may be passed through a slot and secured with a knot or connector 22, or in clips 42 as described below and shown in FIG. 7. While a single wrist strap 20/20a is shown in FIGS. 1-5 and 10, one or more additional wrist straps may be added through other of multiple attachment slots 18 to increase security. Alternative adjustable outer and inner wrist ties 22a and 22b, respectively, are shown in FIG. 2. Wrist straps may optionally be provided with slip-on pads to further disburse pressure on the hand resulting from patient movements.

Shell 12 may be made of a variety of materials. While not strictly required, it is preferred if the cover has some degree of compliancy to reduce chance of injury to a patient that is active or attempts to remove the restraint. A stiff vinyl material between about ⅛ inch to about ¼ inch in thickness is one suitable material option. Additionally, optional outer cage 24 may be provided around all or a portion of cover 12 for increased protection.

To facilitate patient comfort, particularly for patients that are conscious and aware of their surroundings, an interactive activity sensor/switch pad 25 may be provided inside cover 12 at a position within easy reach of the patient's fingers as shown in FIG. 2. Such a switch pad may include, for example, a nurse call button, controls for the room AV system, and/or a PCA button, or controls for any other devices that would ideally be controlled by a conscious patient in various circumstances. Activity and interactivity sensors 26, 28 for video control and patient monitoring also may be integrated into or disposed on cover 12. Also shown in FIG. 2 is attachment 30, which may be used for attachment to a restraint arm as elsewhere described herein. In some embodiments it may be desirable if attachment point 30 is a swivel and rotating ball bearing attachment member.

As a further means of limiting or permitting controlled movement, slots 18 may be used for attachment of arm motion restricting elements such as resistance bands 32 or more inflexible, "rigid" strap connectors 34. Each of resistance band 32 or strap connector 34 may be secured opposite its attachment to cover 12 to a fixed structure such as the patient's bed. Resistance band 32 can allow for controlled movement and exercise. "Rigid" as used herein in connection with straps means inextensible or refers to the limitation on stretch such that movement can be fixed in at least one direction, that of pull against the strap. In this regard, "rigid" is used only as a distinction from stretchable materials such as resistance bands. Thus, when "rigid" strap connector 34 is attached between cover 12 and the patient's bed, movement of the hand and arm can be restricted as needed. (An example of rigid strap connector 34 being secured to the bed is shown in FIG. 8.)

Figure 6:
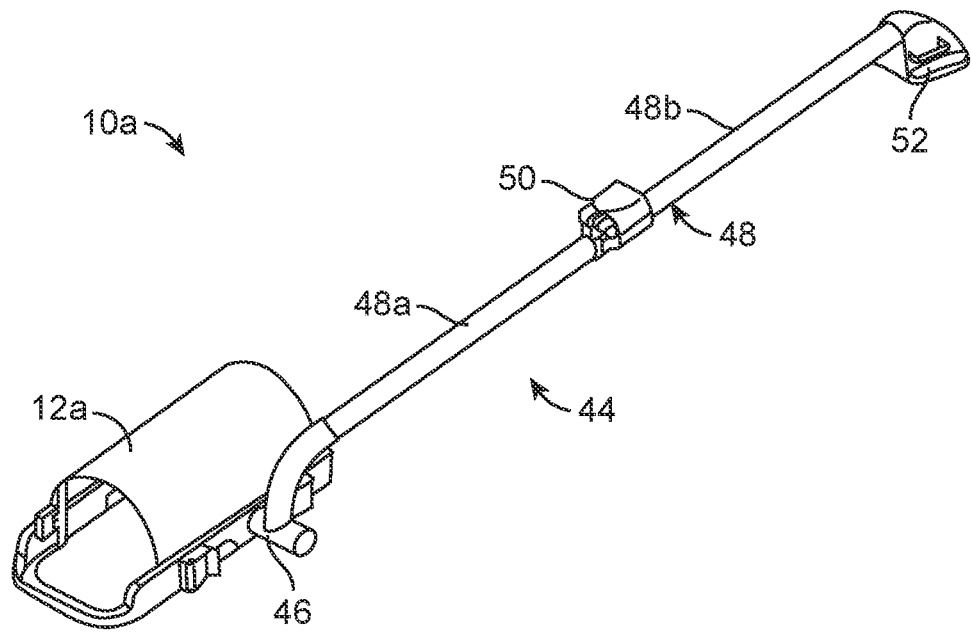
FIG. 6 is a perspective view of an alternative embodiment of a protective and exercise hand restraint in accordance with the present disclosure.
Figure 7:
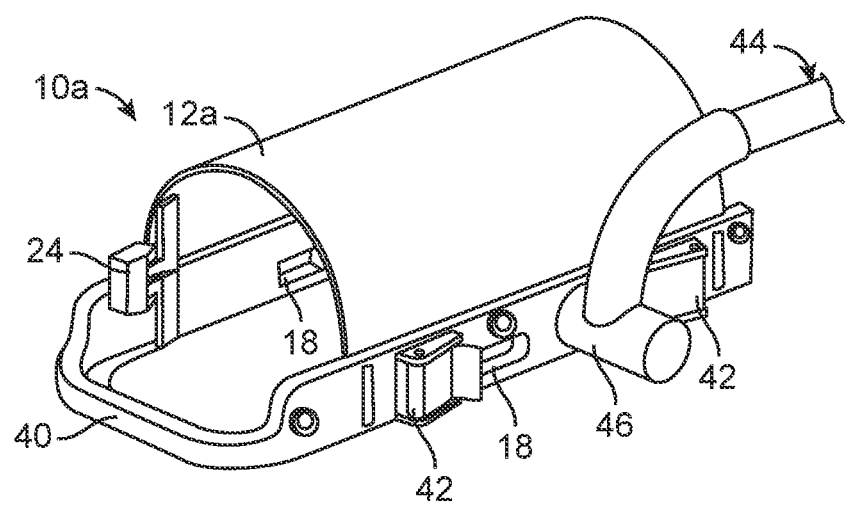
FIG. 7 is a detailed perspective view of the hand cage portion of the restraint shown in FIG. 6.

An alternative embodiment of a protective and exercise hand restraint is shown in FIGS. 6 and 7. In this embodiment, restraint 10a includes cover member 12a supported on frame 40, which may be substantially rigid and generally u-shaped. The padded/soft hand support on which the hand rests (e.g. support 14 in FIG. 1) is not shown in FIGS. 6 and 7, however is removably attached to the underside of frame 40, such as by clips, snaps, hook and loop fastener or other suitable removable attachment means. Slots 18 for strap attachment are provided in frame 40. In this embodiment switch 24 is provided as a two button switch. Additionally, strap clips 42 may be provide on the sides of frame 40 as alternative strap fixation points. These may be used to secure the wrist strap or resistance bands or rigid connector straps as described above.

Restraint 10a is shown here with telescoping restraint arm 44 attached to frame 40 by pivotable connection 46. Telescoping restraint arm 44 includes rigid arm 48 made up of telescoping sections 48a and 48b, which are locked by locking mechanism 50. A variety of commercially available telescoping member lock mechanisms may be employed. Shoulder or upper arm attachment pad and strap 52 is provided at the upper end of rigid arm 48. This allows secure attachment to the patient's upper arm, which allows for limited mobility as may be controlled by straps or resistance bands. Restraint arm 44 also may be covered with a soft protective sleeve, such as a neoprene sleeve to reduce chances of patient injury.

Figure 8:
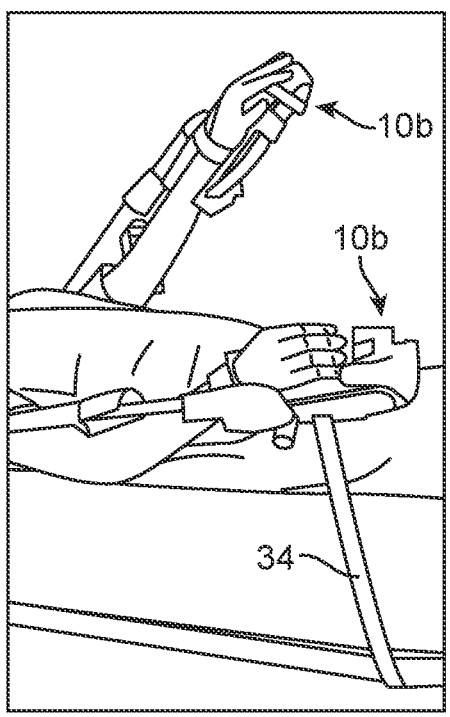
FIG. 8 is a photograph showing a patient fitted with two protective and exercise hand restraints according to the present disclosure.
Figure 9:
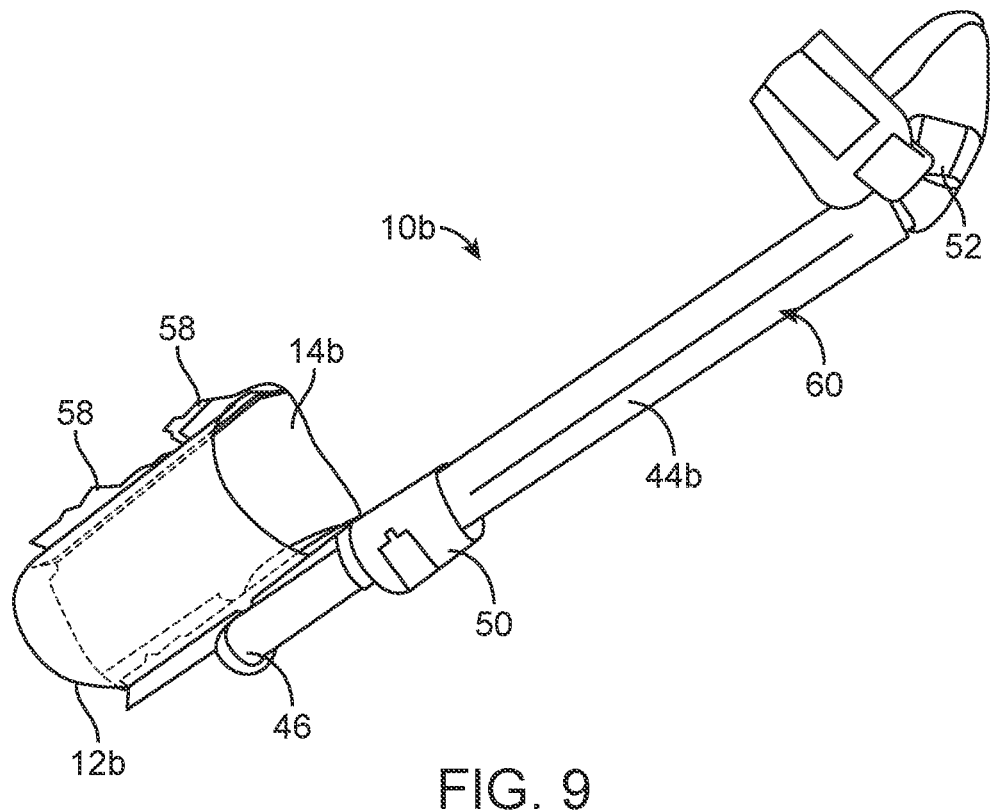
FIG. 9 is a photograph of a further alternative embodiment of a protective and exercise hand restraint in accordance with the present disclosure.
Figure 10:
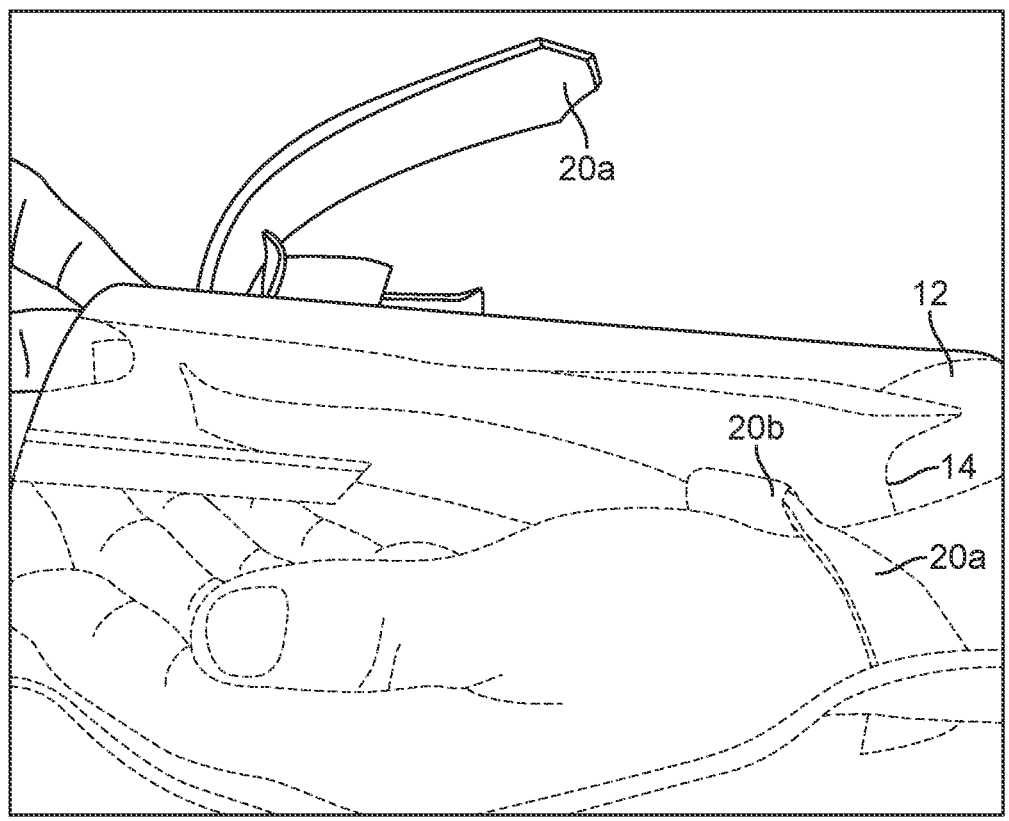
FIG. 10 is a photograph from a top view of an alternative wrist strap with a "noose" configuration in one embodiment of a protective and exercise hand restraint according to the present disclosure.

A further alternative embodiment of protective and exercise hand restraint is shown in FIGS. 8 and 9. In this embodiment, restraint 10b includes a cover 12b formed as a half-tube type structure open at the bottom. Hook and loop fastener type connectors 58 are secured to the sides of cover 12b, which allows soft hand support 14b to be secured across the bottom and securely but removably attached by hook and loop connectors 58. Other features of restraint 10b are generally as described above. Telescoping restraint arm 44b is attached to cover 12b by pivotable connection 46. In this case restraint arm 44b is shown covered by neoprene protective sleeve 60.

FIG. 8 illustrates the mobility and restraint options for patients using restraint embodiments as described herein. In this illustration, restraint 10b is shown but any of restraints 10, 10a or 10b, or other variations consistent with the present disclosure may be employed in the same manner. In FIG. 8, on the patient's left arm, restraint 10b is secured at the shoulder via shoulder strap 52 at the end of restraint arm 44b. The left arm, however, is not otherwise secured against motion and the patient is able to lift the arm at the shoulder to provide motion for exercise and comfort. The fingers remain free, but protected as surrounded by cover 12b. On the patient's right side, restraint 10b is restricted to limited movement by "rigid" connector strap 34, which is connected between cover 12b and the patient's bed.

In another aspect of the present disclosure, methods are provided for protection and/or exercise of intubated patients while maintaining the patient's hand within protective hand restraints. In one embodiment, such a method may include steps of restraining one or both of a patient's hands atraumatically within a hand restraint comprising a padded hand support member covered by a clear cover member extending over the padded hand support member to define a hand receiving opening. The hand receiving opening may be configured and dimensioned so that the cover member does not contact the hand with the hand positioned centrally on the padded hand support member. Such a hand restraint may optionally include additional features or structures as described hereinabove for alternative hand restraint embodiments. With the patient's hand remaining secured within the hand restraint, the method further includes accessing the patient's fingers, back of hand or wrist through an open end of the hand restraint as clinically required for diagnostic or therapeutic intervention. In a further step, the patient's arm motion may be selectively restricted or permitted by securing extensible or inextensible arm restricting elements between the hand restraint and a fixed structure.

Additional, optional method steps may include limiting the patient's hand movement by securing a substantially rigid restraint arm between the hand restraint and the patient's shoulder or upper arm and/or facilitating arm exercise of the restrained patient without removing the patient's hand from the hand restraint by securing a resistance band between the hand restraint and a fixed structure.

Assessments and interventions are thus permitted without removal of the hand restraint(s). Such assessments or interventions may include, for example, viewing of hand through the clear cover member for evaluation of patient conditions such as circulatory color, dislodgement of catheters, lesions/bruising without removing the patient's hand from the hand restraint, or performing at least one of contact monitoring, diagnostic or therapeutic intervention including at least one of pulse oximeter monitoring, fingerstick glucose check, capillary refill check, hand holding, back-of-hand IV placement, arterial line placement or monitoring of placed lines without removing the patient's hand from the hand restraint.

Disclosed embodiments may be made from conventional and readily available, medically-approved materials such as sensors, cottons, elastic fabrics, neoprene, acrylics and plastics, which are latex-free, MRI and other diagnostic imaging-friendly, potentially disposable, lightweight, comfortable, quickly and easily attachable and detachable, sturdy, padded, and cleanable. The arrangement prevents patient removal of the device or of the device on the opposite hand and hinders contact of the hands onto a tube for removal when used as a separate restraint and prevents placement of the hand to the face to remove a tube, for example whether or not used with the tube guard described in the ENDO-TRACHEAL TUBE GUARD application. While primarily described herein in the context of intubated patients, persons of ordinary skill in the art will appreciate that disclosed embodiments are equally applicable for protection of patients who are intubated or otherwise invasively connected to medical support or diagnostic devices.

In one example of use of disclosed embodiments, a medical staff person places the patient's hands in the devices (one per hand) with the wrist tie wrapped around the hand such that there is a single band across the posterior wrist which crosses at the anterior wrist and threads through the hand cage slots to adjustably secure at the outside surface of the hand cage with the palm facing medially without contact of the hand with the hand cage. An optional wrist tie spacer may be used as needed on the inside surface of the hand cage to assure the hand is not in contact with the hand cage while rendering the wrist strap opening too small to allow the hand to be removed through it. The patient can neither grasp tubes and lines on or near the body nor remove the device itself. Movement and exercise are encouraged by full range of motion at the wrist, use of the optional resistance band, movement of the arms if not rigidly tied, and/or use with the activity sensor with interactive video therapy sessions and games.

As may be apparent to persons of ordinary skill, embodiments of the disclosed systems allow for three levels of restraint, all of which prevent the awake and so-inclined subject from disengaging from the restraint or approximating the face and hand, including one configuration for resistance exercise therapy, one configuration for use with interactive video therapy and one configuration for anxiety and agitation monitoring. When used in conjunction with devices disclosed in the ENDOTRACHEAL TUBE GUARD application, there is increased hindrance for self-extubation. Other advantages of the disclosed systems include providing a safe level of freedom and exercise while preventing self-extubation and self-removal even by the agitated or determined patient, providing continual access to back of hand intravenous lines and wrist arterial lines and for skin assessment, full visualization of the hand, reduction of pressure ulcers, with simultaneous prevention of the confused or agitated patient from disengaging the hand and subsequently the restraint on the opposing arm even while in the untied, more liberal configuration. Disclosed embodiments allow rotation of the wrist such that the patient can change wrist position by twisting it as desired and have padding on the outside of the hand cage to prevent harm from contact under velocity to staff, visitor or patient while not interfering with hand cage transparency and visualization of the contained hand.

Embodiments disclosed are configured to accommodate most hand sizes, may be quickly converted to three or more levels of restraint, and affords 360 degree skin assessment and reduced risk of pressure sores of the wrist, hand and underside of the arm or has an exercise modality (resistance bands) or quickly and easily interchange between three levels of restraint.

Further features of the disclosed embodiments include:

Securable at three or more levels of hand restraint (i.e. "secure tri-plus level hand restraint").

Secure tri-plus level hand restraint with an anxiety-reducing intermediate movement and exercise configuration that allows mobility and resistance exercise therapy at multiple levels which can be utilized when the untied (to the bed or chair) state is too risky and the rigid tie (to the bed or chair) is too strict or anxiety provoking and/or if the patient can exercise, whether knowingly or unknowingly in order to accommodate the ever-changing needs of the intubated patient promoting minimal levels of both restraint and sedation necessary while disallowing self-removal by the so-intentioned patient.

Secure tri-plus level hand restraint which is attachable by a hinging ball-bearing securing mechanism to the wrist portion of the arm restraint rod allowing rotational movement at the wrist and allowing a medical staff person to hinge the hand cage upward and detach the under wrap, for enhanced access to the hand, disallowing patient approximation of face and hand.

Secure tri-plus level hand restraint that, through a sensor, wirelessly monitors patient motion, anxiety and agitation.

Secure tri-plus level hand restraint that, through a sensor and switch pad, interacts with video therapy sessions and games, alerts with patient requests, interacts for communication, on-screen photo album control, video calls, and/or performs other functions.

Secure tri-plus level hand restraint which by its hand cage design disallows self-removal of the fingers and hand by the fully awake and so-intentioned patient for interference with lines and tubes even when not tied to the bed or chair thereby hindering self-extubation and allowing minimized sedation.

Secure tri-plus level hand restraint with continual visibility of hand for intravenous and intra-arterial line sites, edema, discoloration, and circulation assessment and monitoring.

Secure tri-plus level hand restraint with padding on the outside of the transparent, mesh-ventilated hard-shell hand cage to substantially reduce harm from contact under velocity.

Secure tri-plus level hand restraint with lack of circumferential binding and non-interference with hand and wrist venous and artery line sites.

Secure hand restraint with minimization of skin contact for non-interference with skin integrity.

Secure tri-plus level hand restraint which, when combined with devices disclosed in the ENDOTRACHEAL TUBE GUARD application, enhances prevention of dislodging an endotracheal tube by inhibiting squeezing around the ETT for removal.

Using systems disclosed herein, a single device may be effectively employed for many levels of restraint desired throughout a patient's changing status promoting minimal restraint necessary. Disclosed systems provide unique features that prevent self-extubation while not strapped to a bed or chair for an awake and at-risk patient who might otherwise wriggle out of a palm strap, and encourage early mobilization and exercise promoting the strength required for advancement from the ventilator. Embodiments do not inflict pressure on the underside of the hand or arm thereby reducing the risk of pressure sores and skin breakdown and expose the back of the hand and anterior wrist for intravenous and intra-arterial lines, also optimizing skin integrity in this area. The multiple degrees of increased freedom of movement provided by disclosed systems allow for reduced patient agitation and therefore sedation medication may be decreased and minimized which in turn promotes increased patient cognition and thereby would be more likely to reduce the incidence of delirium and post-ICU syndrome, a form of PTSD. Once a patient-appropriate restriction configuration is in place, direct nurse or sitter monitoring may not be necessary whereas untying the restraints currently available without constant 1:1 supervision invites self-extubation.

Figure 2:
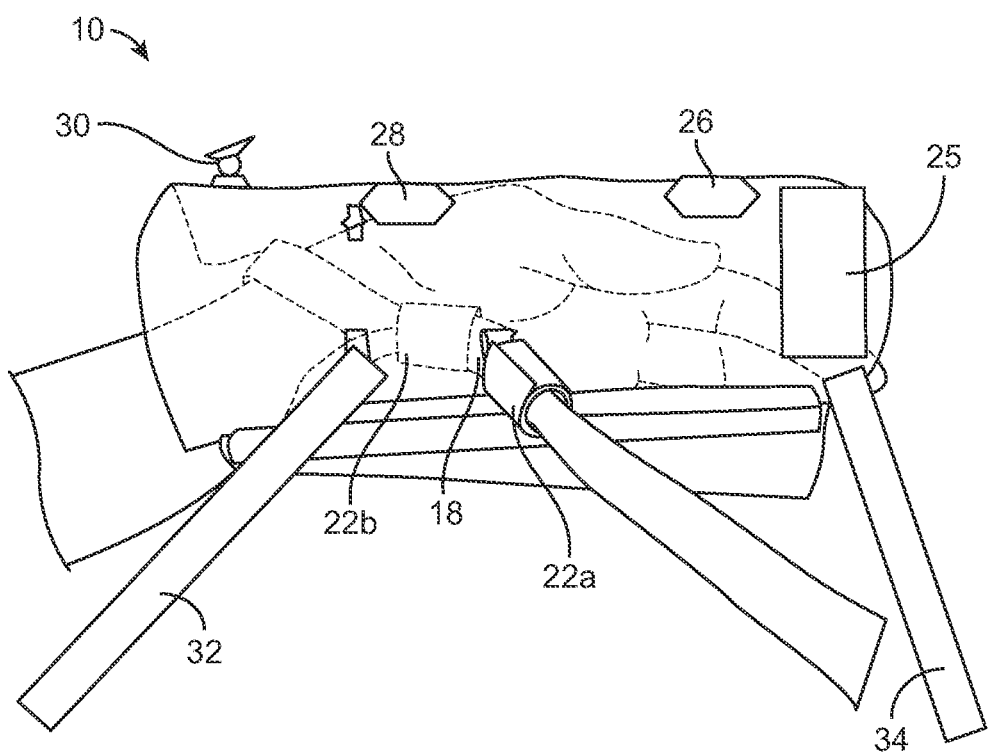
FIG. 2 is a photograph of the protective and exercise hand restraint as viewed from the left-handed medial palmar side of the single slot embodiment made in accordance with the present disclosure.
Figure 3:
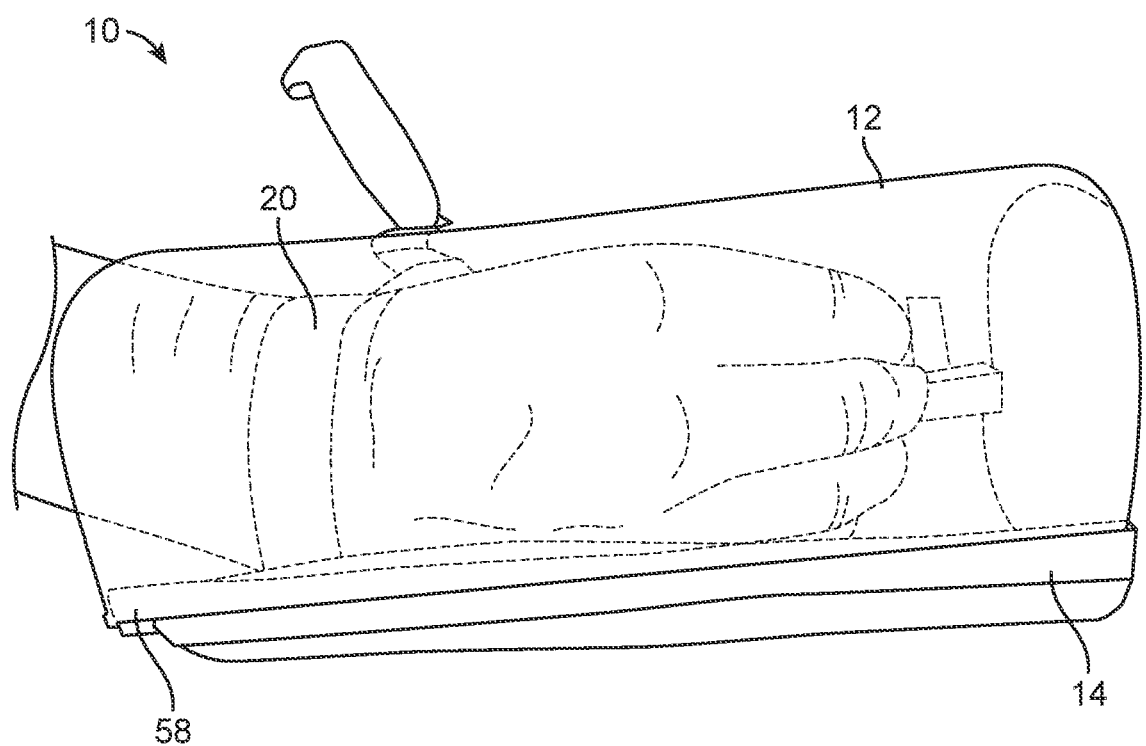
FIG. 3 is a photograph of a hand cage as viewed from the lateral back side made in accordance with the present disclosure.
Figure 4:
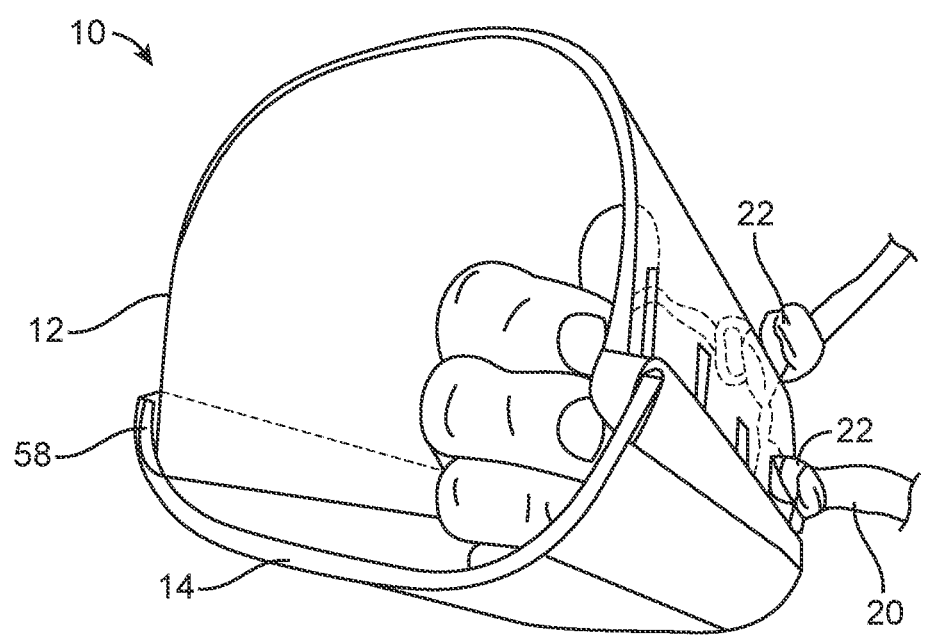
FIG. 4 is a photograph of the hand cage as viewed from the bottom anterior side made in accordance with the present disclosure.
Figure 5:
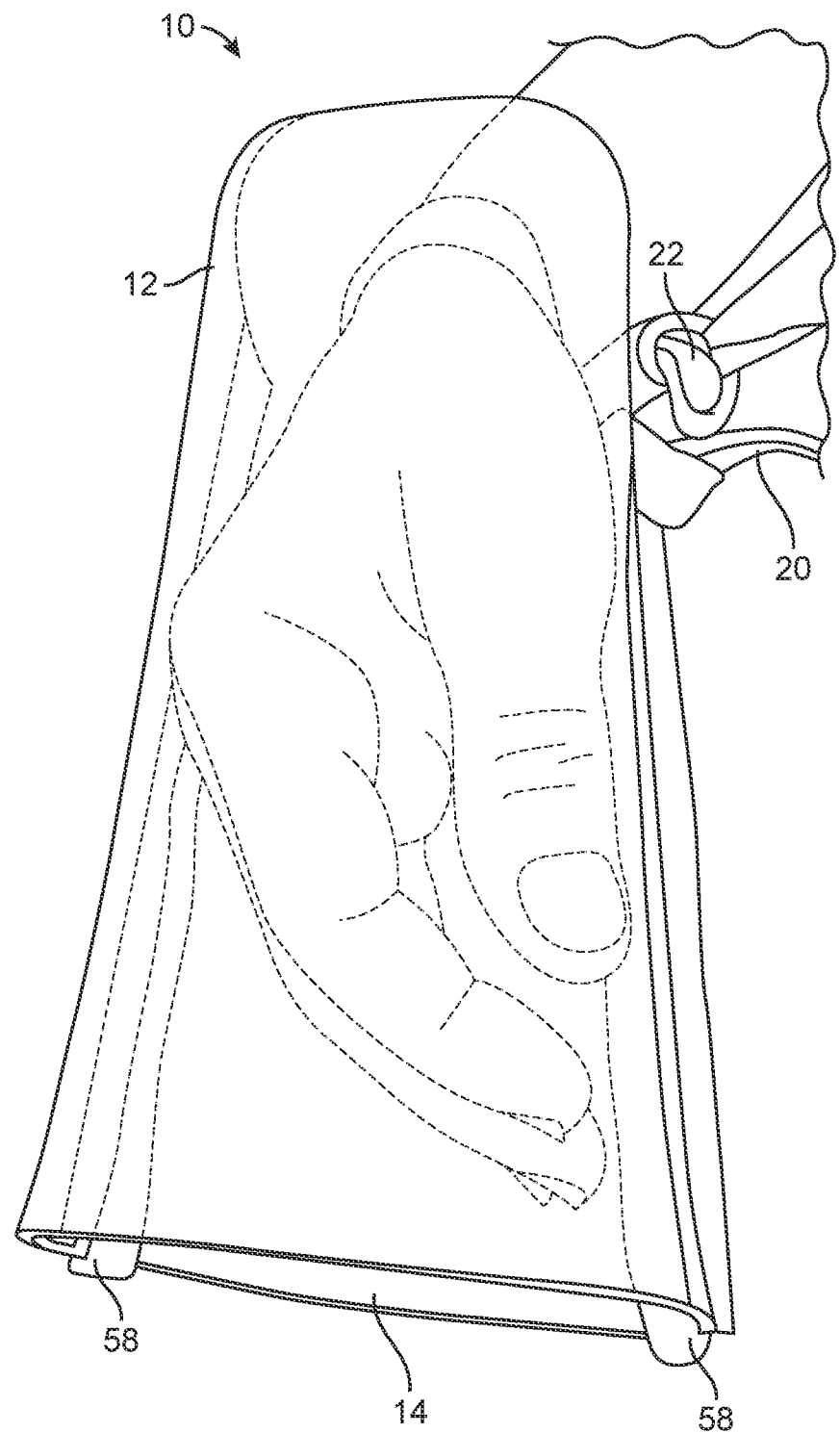
FIG. 5 is a photograph of a hand cage as viewed from the top made in accordance with the present disclosure.

Prototypes of the dual and single slot embodiments, shown in FIGS. 1 and 2, were tested on male and female test subjects under simulated clinical conditions. The prototypes shown in FIGS. 1 and 2 were placed on awake male and female non-intubated healthy subjects ranging in age from 25-40 and heights of 5'2" to 5'10". During this testing it was determined that in the un-tied state, the lack of freedom of the hand in the wrist tie attached to the hand cage prevented removal of the device or removal of the device on the opposing hand. Subjects were unable to grasp anything outside of the hand cage. The tested devices accommodated the variable hand sizes in this height category for these subjects. Non-circumferential banding at the wrist did not interfere with circulation. In the resistance band tie configuration, enhanced exercise was possible by moving the arms without being able to reach an object placed on the face or torso. In the rigid tie configuration, it was possible to bend the face to the hand cage but not to the hand. The device was described by test subjects as being comfortable.

Exemplary embodiments have been disclosed above and illustrated in the accompanying drawings. It will be understood by those skilled in the art that various changes, omissions and additions may be made to that which is specifically disclosed herein without departing from the spirit and scope of the present disclosure.

What is claimed is:

1. A protective and exercise hand restraint, comprising:
    a padded hand support member;
    a cover extending over the padded hand support member to define a hand receiving opening, said opening being configured and dimensioned so that the cover does not contact the hand with the hand positioned centrally on padded hand support member, said hand receiving opening being open at each end; and
    at least one wrist attachment configured to surround the wrist and secure the hand within the hand receiving opening by tightening in response to attempted withdrawal of the hand from the restraint and loosening in response to opposite motion;
    wherein said at least one wrist attachment comprises at least one strap configured with a slip loop configured to be positioned around a patient's wrist with the patient's hand in the restraint.

2. The hand restraint of claim 1, wherein said hand-receiving opening defined by the padded hand support member and the cover provides sufficient space to allow access to a hand positioned in the restraint to permit diagnostic or therapeutic interventions to be performed on the back of the hand, wrist or fingers without removing the hand from the restraint.

3. The hand restraint of claim 1, further comprising plural slots in said cover through which said at least one wrist attachment or an arm motion restricting element may be passed and secured.

4. The hand restraint of claim 1, wherein said at least one wrist attachment comprises a webbing strap and said restraint further comprises clips mounted to secure the webbing.

5. The hand restraint of claim 1, wherein said cover is clear to permit observation of the patient's hand without removal from the restraint.

6. The hand restraint of claim 1, further comprising an activity control switch positioned on a medial side, inside of the cover in a position accessible to the patient's fingers when the hand is secured in the restraint.

7. A protective and exercise hand restraint, comprising:
    a padded hand support member;
    a cover extending over the padded hand support member to define a hand receiving opening, said opening being configured and dimensioned so that the cover does not contact the hand with the hand positioned centrally on padded hand support member, said hand receiving opening being open at each end;
    at least one wrist attachment configured to surround the wrist and secure the hand within the hand receiving opening by tightening in response to attempted withdrawal of the hand from the restraint and loosening in response to opposite motion; and
    a substantially rigid frame member positioned between the cover and padded hand support, wherein attachment means for the padded hand support are positioned on the said frame member;
    wherein said at least one wrist attachment comprises at least one strap configured with a slip loop configured to be positioned around a patient's wrist with the patient's hand in the restraint.

8. The hand restraint of claim 7, wherein the cover is a soft, clear, compliant material supported by said substantially rigid frame member.

9. The hand restraint of claim 7, further comprising a pivotable attachment on the frame member configured for attachment of a restraint arm.

10. The hand restraint of claim 7, further comprising an elongated, substantially rigid restraint arm secured to said frame member.

11. A protective and exercise hand restraint, comprising:
    a padded hand support member;
    a cover extending over the padded hand support member to define a hand receiving opening, said opening being configured and dimensioned so that the cover does not contact the hand with the hand positioned centrally on padded hand support member, said hand receiving opening being open at each end;
    at least one wrist attachment configured to surround the wrist and secure the hand within the hand receiving opening by tightening in response to attempted withdrawal of the hand from the restraint and loosening in response to opposite motion; and
    a pivotable attachment member disposed on the cover for attachment of a restraint arm;
    wherein said at least one wrist attachment comprises at least one strap configured with a slip loop configured to be positioned around a patient's wrist with the patient's hand in the restraint.

12. The hand restraint of claim 11, wherein said restraint arm is telescoping for length adjustment and includes a shoulder or arm attachment opposite said hand restraint.

* * * * *